United States Patent [19]

Stracher et al.

[11] Patent Number: 4,866,040

[45] Date of Patent: Sep. 12, 1989

[54] AMINOCARNITINE DIRECTED PHARMACEUTICAL AGENTS

[76] Inventors: Alfred Stracher, 47 The Oaks, Roslyn Estates, N.Y. 11576; Leo Kesner, 1726 E. 32nd St., Brooklyn, N.Y. 11234

[21] Appl. No.: 3,888

[22] Filed: Jan. 15, 1987

Related U.S. Application Data

[63] Continuation-in-part of Ser. No. 816,546, Jan. 6, 1986, Pat. No. 4,742,081.

[51] Int. Cl.[4] ............... A61K 31/225; A61K 37/02; A61K 37/64; C08G 69/08
[52] U.S. Cl. ............................. 514/17; 424/450; 428/402.2; 514/2; 514/78; 514/305; 514/535; 514/547; 514/556; 514/821; 530/330
[58] Field of Search ............ 514/547, 305, 535, 547, 514/556, 821, 2, 17; 428/402.2; 530/330

[56] References Cited

U.S. PATENT DOCUMENTS

| | | | |
|---|---|---|---|
| 3,929,756 | 12/1975 | Leeman et al. | 530/327 |
| 3,998,790 | 12/1976 | Brändström et al. | 514/821 X |
| 4,320,110 | 3/1982 | DeFelice | 514/34 X |
| 4,327,725 | 5/1982 | Cortese et al. | 424/473 X |
| 4,401,827 | 8/1983 | DeWitt | 560/55 X |
| 4,440,740 | 4/1984 | Fix et al. | 424/1.1 |
| 4,443,475 | 4/1984 | Cavazza | 514/821 X |
| 4,537,772 | 8/1985 | Alexander et al. | 514/556 X |
| 4,742,081 | 5/1988 | Stracher et al. | 514/547 |

*Primary Examiner*—Richard D. Lovering
*Attorney, Agent, or Firm*—Sprung Horn Kramer & Woods

[57] ABSTRACT

Carnitine, aminocarnitine and cysteic acid serve as carriers to bring pharmaceutically active compounds to desired sites in the body, e.g. skeletal muscle or the heart. The pharmaceutically active compound can be a protease inhibitor, a cardioactive drug for combating arrythmia, etc. The linkage is chemical through one or more alcohol, carboxyl or amine groups using reagents such as glutaraldehyde, dicarboxylic acid anhydrides and acid halides and carbodiimides. Carnitine derivatives are also incorporated into liposomes which are then used as carriers of active pharmaceutical agents.

16 Claims, No Drawings

AMINOCARNITINE DIRECTED PHARMACEUTICAL AGENTS

This application is a continuation-in-part of pplication Ser. No. 816,546, filed Jan. 6, 1986, now U.S. Pat. No. 4,742,081.

The present invention relates to the provision of novel pharmaceutically active compounds which will preferentially be delivered to preselected sites in the patient's body, and to intermediate therefor.

It is known that certain compounds when administered to patients preferentially concentrate in selected tissues.

It is also known that 1-carnitine, a compound of the formula

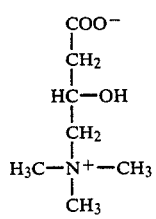

and commercially available in large quantity is readily concentrated by active transport in cardiac and skeletal muscle at 50-100 times the concentration found in plasma. The physiological function of carnitine is to transport long and short chain fatty acids into cells and across mitochondrial membranes bound through an ester linkage.

Finally it is known that certain compounds are protease inhibitors. Leupeptin is one such material, as described in U.S. Pat. No. 4,510,130, issued Apr. 9, 1985.

Artificial lipid membrane vesicles, commonly known as liposomes, have been intensively studied for use as carriers for delivery of drugs and proteins to various tissues and tumors (Ostro, M.,ed. *The Liposomes*, Marcel Dekker, N.Y., 1983; Knight, C. G., ed. *Liposomes: From Physical Structure to Therapeutic Applications*, Elsevier/- North Holland Biomedical Press, New York, 1981; Gregoriadis, G. ed. *Liposome Technology, Vol.* 1-3, CRC Press, Inc., Boca Raton, Fla., 1984).

It is accordingly an object of the invention to utilize these concepts and provide pharmaceuticals which, though not per se selectively deliverable, can be rendered selectively deliverable to predetermined tissues.

It is a further object of the invention to provide pharmaceuticals which are preferentially deliverable to cardiac and skeletal muscle.

These and other objects and advantages are realized in accordance with the present invention pursuant to which compounds which upon administration preferentially concentrate in certain tissues, and are utilized to carry pharmaceutically active compounds to such sites. This carrier action is accomplished by providing a chemical linkage which does not markedly interfere with either the carrier action or pharmaceutical activity.

In accordance with one aspect of the invention, the carrier is a compound which preferentially travels to cardiac and skeletal muscle, e.g., carnitine of the formula

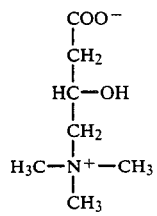

Advantageously this is linked through the hydroxyl group, preferably as an ester, to a pharmaceutically active material, e.g., leucyl argininal for the formula

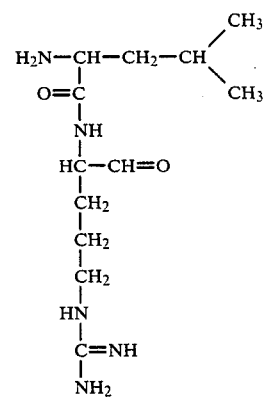

The linkage is preferably through the amino group which is connected to a —CH— radical, by means of a bifunctional radical. Thus, the carnitine and leucyl argininal can be linked by a polyfunctional reagent, the carnitine can be esterified with an acid carrying a functional group and then this functional group and the NH$_2$ of leucyl argininal can be linked, or the leucyl argininal can be reacted with a reagent carrying a second functional group and this can be linked to the carnitine in the next step. If desired or necessary, other reactive sites may be temporarily blocked.

In this approach, advantageously the carnitine is first esterified, preferably with an aminoalkanecarboxylic acid or perhaps an alkanedicarboxylic acid, leaving an amine or carboxyl group hanging free. Then this is joined to the pharmaceutical by a bifunctional reagent such as a dialdehyde, e.g., glutaraldehyde, a carbodiimide, a diisocyanate, and the like. In other words, the linkage between the two ends of the new molecule may be in one step, or in two or more steps. The connector can be aliphatic or aromatic and can be substituted in the chain or on the side. Substitutions in the chain can result from the use of particular linking agents such as those carrying amino, carboxyl, carbonyl, alcohol and- /or thiol groups, amino and carboxyl being preferred.

In accordance with another aspect of the invention, the protease inhibitor linked to the carnitine can be pepstatin, of the formula

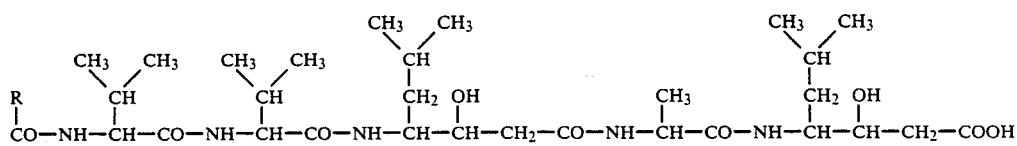

where R may be:

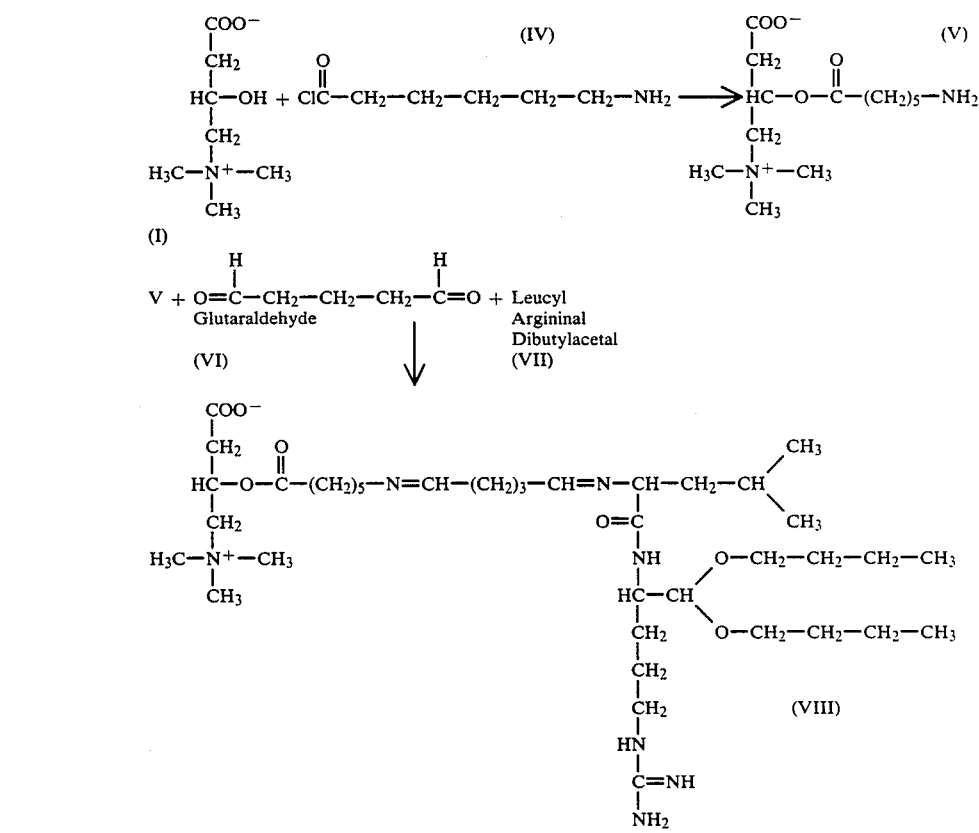

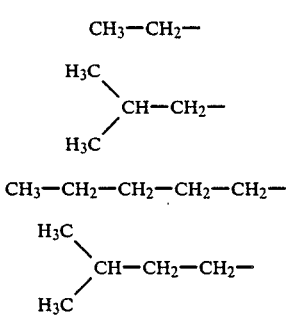

Advantageously aside from connecting functional groups as described above, the linkages involve lower aliphatic radicals, i.e., containing up to about 22 atoms. A suitable first reagent is ε-aminocaproic acid, which is readily available commercially. Ester formation with carnitine (I), for example, will proceed by reacting with the acid chloride of ε-aminocaproic acid (IV). The ester is then joined to leucylargininal dibutylacetal by glutaraldehyde to produce compound VIII. The Schiff base can then be reduced with $CNBH_4$ and the dibutylacetal cleaved at pH 2 for 3 hours at 60° C. The final active compound is isolated by Sephadex G-10 chromatography.

In a similar way carbodiimide can be used in place of glutaraldehyde as the linking agent using glutaric acid as a connector. Thus the carnitine can be linked to the leucyl argininal by an alkylene-X-alkylene linkage, wherein X is —N—, —NH—, —NH—NH—, —O—, —S—, —COHN—, or the like, the two ends being sufficiently spaced so as not to interfere with one another biologically.

The leucyl argininal starting material is prepared from leupeptin.

It is now known if the activity is because the carnitine or other carrier permits the leucyl argininal to be present at a site in high concentration whereas the unlinked leucyl argininal itself cannot reach a therapeutic level.

Other protease inhibitors or precursors thereof, such as pepstatin, bestatin, antipain, Bowman-Burk inhibitor, benzamidine derivatives, chymostatin, bacitracin, or the like, can also be employed.

Other carriers and other pharmaceutically active compounds can be similarly linked through one or more bridges involving alcohol, carboxyl and/or amine groups.

In accordance with another aspect of the invention, the carrier can be other substances which also preferentially travel to cardiac and skeletal muscle. One such substance is aminocarnitine (IX).

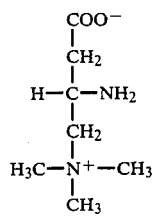

This material is synthesized from 6-(dimethylaminomethyl)uracil as described in Jenkins, D.J. and Griffith, D. W. *J. Biol. Chem.* (1985) 260, 14,748–14,755. This compound and some of its derivatives are non-toxic when fed orally and are excreted unchanged in the urine (*Proc. Natl. Acad. Sci. U.S.A.* (1986) 83, 290∝294.

The amino group on carbon 3 offers a convenient functional group for attaching a host of protease inhibitors and other compounds to this substance with carnitine-like transport properties. The linkage to leucylargininal dibutylacetal(VII) can be made through glutaraldehyde (VI) to form compound (X).

The Schiff base dibutylacetal may be used as is, or reduced with sodium cyanoborohydride at neutral pH followed by cleavage of the diacetal groups at pH 2, 60° C. for 3 hours to form compound (XI) which is the active protease inhibitor.

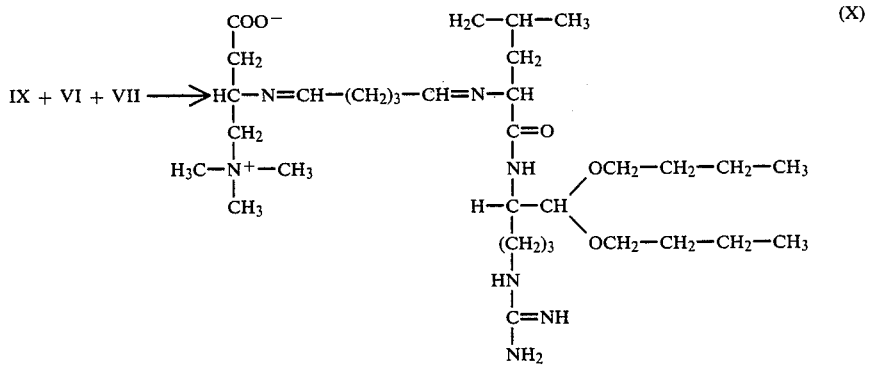

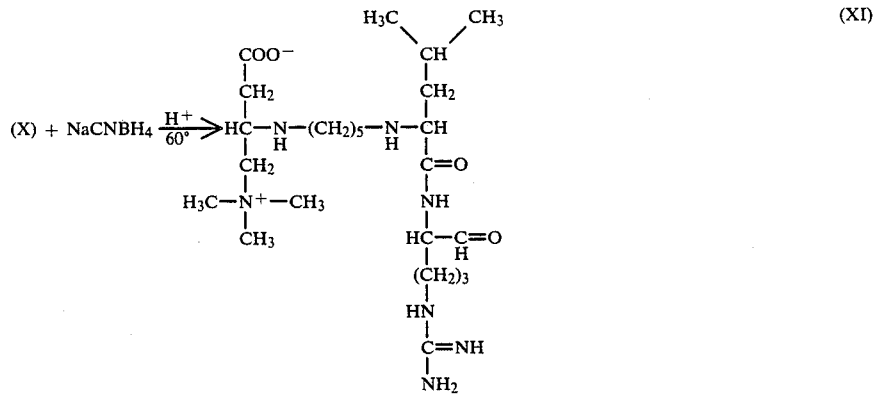

Another way of coupling the amino group of amino carnitine to leucylargininal dibutylacetal is through a carbodiimide procedure similar to that described in Example 3 hereinbelow. Glutaric acid (1 mmole) is reacted with 2 equivalents of 1-ethyl-3-(3-dimethyl aminopropyl) carbodiimide in 2 ml H$_2$O at room temperature for 30 minutes. To this is added 1 equivalent of aminocarnitine and 1 equivalent of leucylargininal dibutylacetal (VII). The substance (XII) is purified by passage through a Sephadex G10 column and fractions are tested for trypsin inhibitory activity following treatment at pH 2 for 3 hours at 60° C. which removes the acetal functional groups to release the free aldehyde which is the protease inhibitor (XIII).

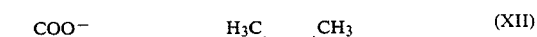

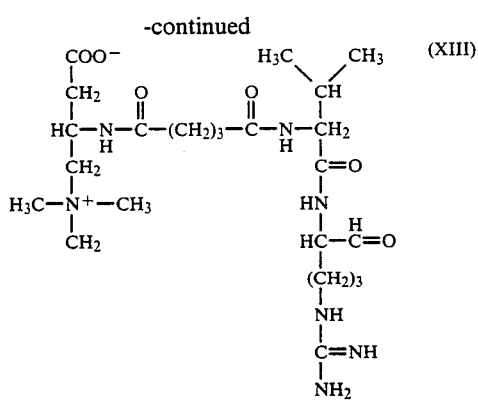

In accordance with another aspect of the invention, other protease inhibitors with available carboxyl functional groups such as pepstatin (III) may be linked directly to the aminocarnitine by means of the carbodiimide reaction. One mmole pepstatin (III) and 1.2 mmoles of 1-ethyl-3-(3-dimethyl aminopropyl) carbodiimide (CDI) in 50% dimethylformamide are reacted at room temperature for 1 hour. To this is added 1 mmole of aminocarnitine and the reaction is allowed to proceed for 12 hours. The product (XIV) is isolated by cation exchange chromatography on Dowex 50x4 using pyridine acetate pH 4.5 as eluting buffer. The tubes containing compound (XIV) are located by thin layer chromatography and by their pepsin inhibitory activity. Pyridineacetate is removed during lyophylization.

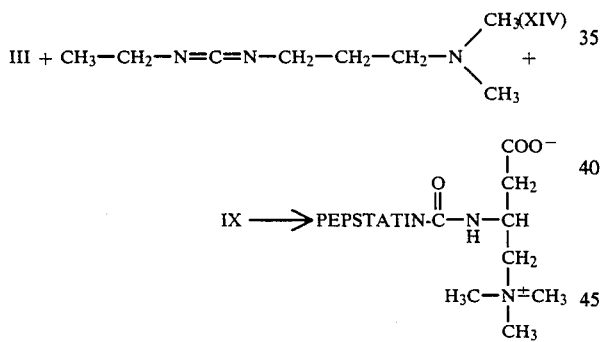

In accordance with another aspect of the invention, the carrier can be another substance which concentrates in cardiac and skeletal muscle. Upon administration of taurine its levels are elevated in skeletal muscle of dystrophic animals (Wilson, B. W., Peterson, D. W. Lilyblade, A. L., *Proc. Soc. Exp. Biol. Med.* (1965) 119, 104), and markedly elevated in hearts suffering from congestive heart failure (Huxtable, R. and Bressler, R., *Biochem. Biophys. Acta* (1973) 323, 573. Taurine also reaches the central nervous system and peripheral nervous system and enters adrenal glands and platelets. A number of substances which are actively taken up by the taurine receptor mechanism have a common structural characteristic which consists of a basic and acidic group separated by 2 carbon atoms, e.g. 2-sulfoethylamine. By providing thereon a further non-interfering functional group, e.g. a carboxyl group, it is possible to employ it as a carrier for pharmaceuticals. One such substance to which we can attach protease inhibitors is cysteic acid (XV).

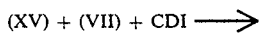

The carboxyl group offers a convenient functional group for attaching a host of protease inhibitors as well as other agents found useful for specific delivery to a variety of tissues such as cardiac and skeletal muscle, nervous tissue, adrenal medulla, platelets etc.

The linkage to leucylargininal dibutylacetal(VII) can be readily made through the carbodiimide reaction. One mmole of cysteic acid (XV) plus 1 mmole of leucylargininal dibutylacetal (VII) are dissolved in 2 ml water and to this is added 1.5 mmoles of 1-ethyl-3-(3-dimethyl aminopropyl) carbodiimide. The reaction is allowed to proceed for 6 hours at room temperature. Isolation of the purified material (XVI) is accomplished by Sephadex G10 chromatography. Peaks are identified by thin layer chromatography and by trypsin inhibitory activity following diacetal cleavage of the acetals at pH 2, 60° C. for 3 hours (XVII).

(XV) + (VII) + CDI ⟶

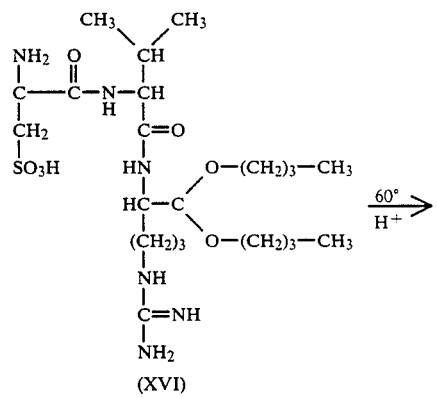

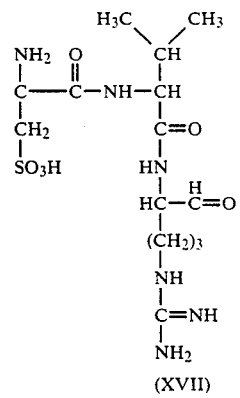

In accordance with another aspect of this invention, preexisting drugs may be attached to a carrier which will more specifically target the drug to a tissue of choice.

An example of this is the combination of antiarrythmic drugs bound to carnitine, aminocarnitine or cysteic acid. The affinity of carnitine, aminocarnitine and cysteic acid derivatives of the antiarrythmic drugs for cardiac muscle, makes them more effective at lower doses and thus reduces the side effects commonly seen with these drugs. Thus, large doses of quinidine are known to produce a syndrome known as cinchonism which is characterized by vertigo, nausea and visual and auditory disturbances. Procainamide, another antiarrythmic has also been shown to produce nausea, vomiting, and diarrhea with large doses. After a while, syndromes resembling systemic lupus erythmatosus and arthralgia may also develop. By making these drugs more specific, lower doses will be needed and thus these side effects may be avoided.

There are more than two dozen antiarrythmic drugs in common usage. These are described in standard textbooks dealing with cardiovascular pharmacology such as B. R. Lucchesi and E.S. Patterson in "*Cardiovascular Pharmacology*" ed. M. Antonaccio, second edition, Ravin Press, N.Y., 1984, pp 329, and A. Scheeweiss, *Drug Therapy in Cardiovascular Diseases*, Lea and Febiger, Philadelphia, 1986.

Antiarrythmic drugs containing alcoholic functional groups such as quinidine (XVIII) and propranolol (XIX) may be coupled to carnitine in several ways.

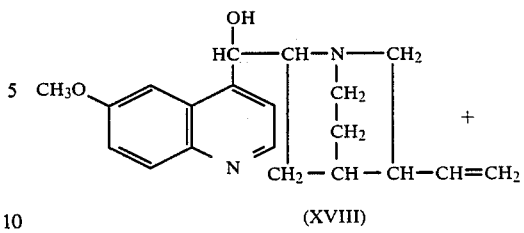

(XVIII)

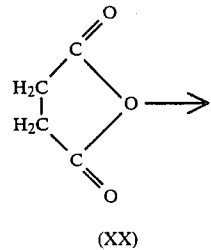

(XX)

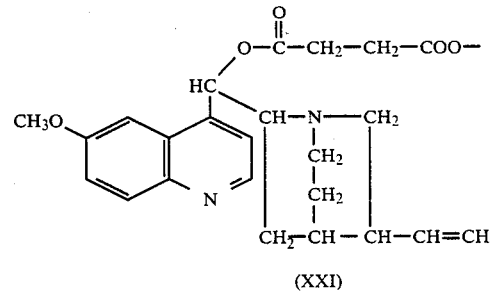

(XXI)

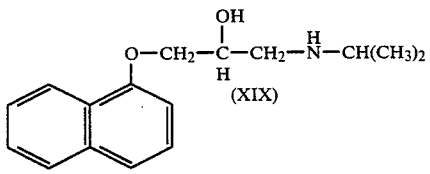

(XIX)

As an example, the formation of a carnitinequinidine complex is described as follows- One mmole of quinidine (XVIII) is refluxed with 1.2 mmoles of succinic anhydride (XX) in pyridine to produce a succinic acid ester of quinidine (XXI).

In a similar manner, 1 mmole of carnitine (I) is refluxed with 1.2 mmoles of succinic anhydride (XX) in pyridine to yield the succinic acid ester of carnitine (XXII).

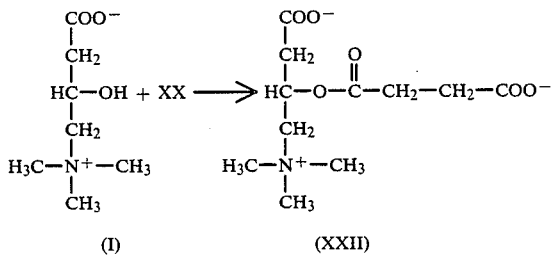

(I)         (XXII)

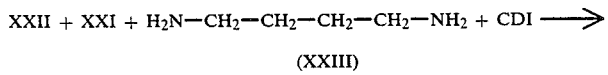

(XXIII)

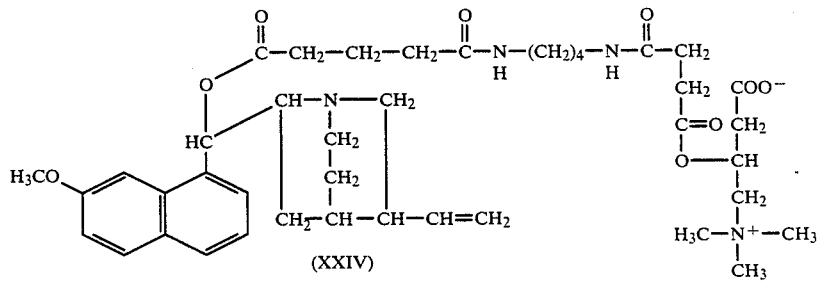

(XXIV)

These two esters are purified by silica gel chromatography using chloroform and butanol gradient. The two compounds, each with a carboxylic group, are now joined by means of a carbodiimide reaction in the presence of a suitable diamino compound such as diaminobutane (XXIII). Other diamino compounds may also be utilized. The new compound XXIV is purified by passage through a Sephadex G10 column.

Another way of coupling hydroxy containing antiarrythmics to carnitine is through use of an alkyldicarboxylic acid halide such as sebacoyl dichloride (XXV).

One mmole of l-carnitine (I) is dissolved in 0.6 mmole of sebacoyl dichloride (XXV) at 4° C. and to this is added one mmole of propranolol (XIX). The carnitine sebacoyl propranolol compound (XXVI) is isolated by Sephadex chromatography.

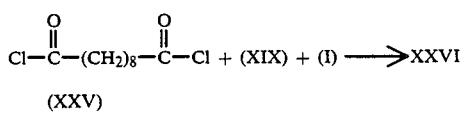

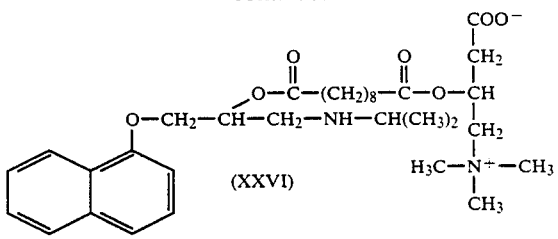

Aminocarnitine can also be coupled to the succinic acid ester of alcoholic antiarrythmics such as quinidine (XVIII) in the following manner. Dissolve (XXI) in dioxane and add an equimolar amount of isobutylchloroformate (XXVII) and triethylamine. A mixed anhydride is formed (XXVIII). To this is added an equimolar amount of aminocarnitine (IX) to yield the derivative (XXIX). This is isolated by silica gel chromatography.

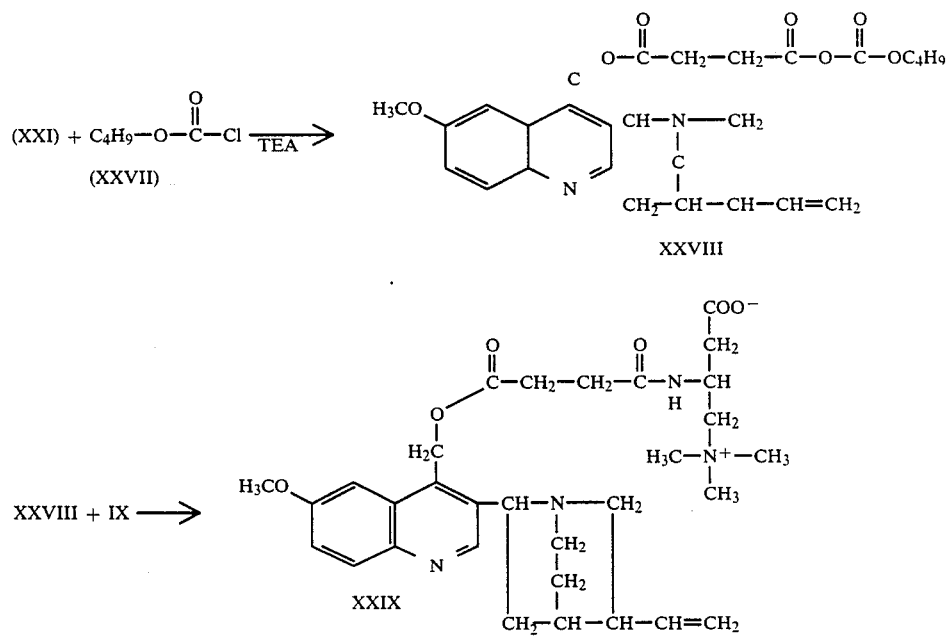

Antiarrythmic agents with a free amino group such as procainamide (XXX) may be coupled to carnitine through use of its succinic acid ester (XXII). By use of the carbodiimide reaction, the free carboxyl group on (XXII) is coupled to the amino group of procainamide. The resulting compound (XXXI) is purified by means of Sephadex chromatography.

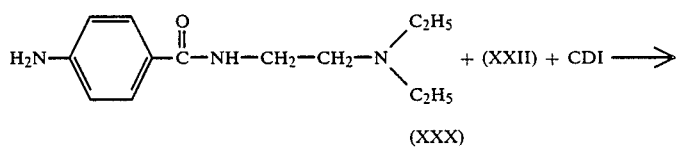

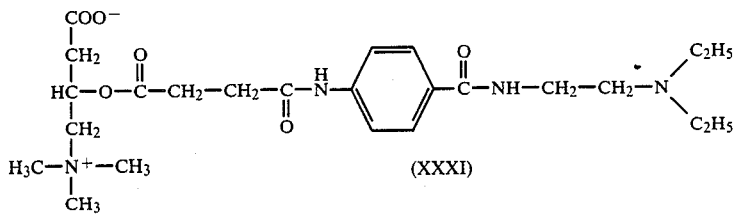

(XXXI)

Procainamide (XXX) can also be linked to aminocarnitine (IX) by means of Schiff base formation through use of glutaraldehyde (VI). This is followed with reduction using cyanoborohydride to yield compound (XXXII).

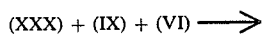

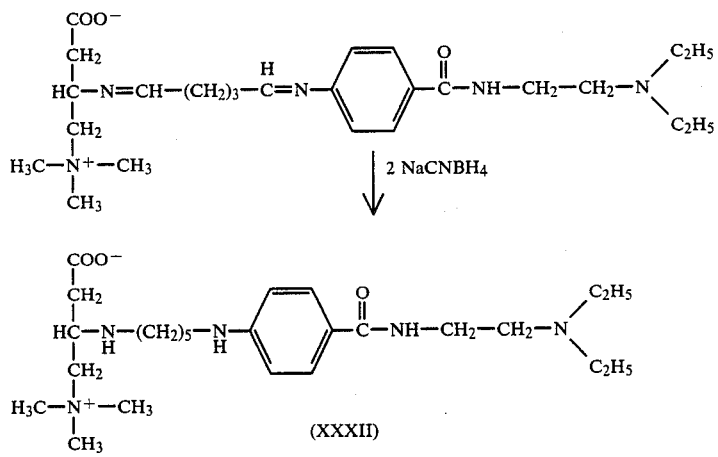

(XXXII)

Procainamide (XXX) can also be linked to cysteic acid (XV) by means of a carbodiimide reaction. One mmole of cysteic acid is reacted with 1.5 mmoles of 1-ethyl-3-(3-dimethylaminopropyl) carbodiimide in the presence of 3 mmoles procainamide in pH 5 phosphate buffer. After 12 hours in the dark, the resulting compound (XXXIII) is purified by Sephadex chromatography.

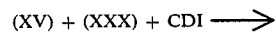

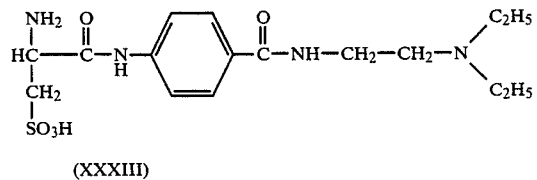

(XXXIII)

In accordance with another aspect of the invention, the carrier which brings the active material to the predetermined site, e.g. carnitine for muscle, can be chemically linked to a phosphatide in the form of a liposome. The pharmaceutically active compound then exists enclosed as an aqueous solution inside the liposome. The chemical linkage between carrier and phosphatic can be direct or indirect, e.g. through a linking agent coupled to the phosphatide and to carnitine, aminocarnitine or cysteic acid.

Carnitine can be incorporated into liposomes in a number of ways and still retain the carbonyl and trimethylamine functional groups needed for the recognition of the carnitine receptor site. One way to do this is to use phosphatidylcarnitine or a mixture of phospholipids and lipids containing some fraction of its components as phosphatidylcarnitine. Phosphatidylcarnitine is synthesized from phosphatidic acid of desired fatty acid composition, optical activity and any other characteristics required. This is then reacted with the phthalimidomethyl ester of carnitine using triisopropylbenzenesulfonyl chloride in pyridine as the condensing agent. The ester protecting group is then removed using sodium thiophenoxide as hydrolyzing agent to yield phosphatidylcarnitine (XXXIV).

The procedure is similar to that described by Browning, J. and Seeling, J., *Chem. Phys. Lipids* 24, 103 (1979) for the synthesis of phosphatidylserine and phosphatidylcholine. Numerous other procedures utilizing other protecting goups and condensing agents have been reported (Chadha, J. S., *Biochem. Piophys. Acta* 248, 455 (1971), Rosenthal, A. F., *Methods in Enzymology* 358, 429 (1975), and Eibl, H. In *Liposomes: From Physical Structure to Therapeutic Applications*, ed. C. G. Knight, Elsevier/North-Holland Biomedical Press, N.Y., 1981 pp19–49. In the following reactions it may be necessary to protect the COO⁻ group of the carnitine moiety with a suitable blocking group as per the more detailed procedure of example 4 (XXXV).

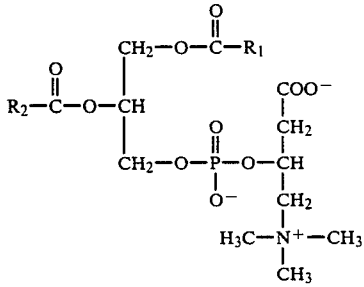

(XXXIV)

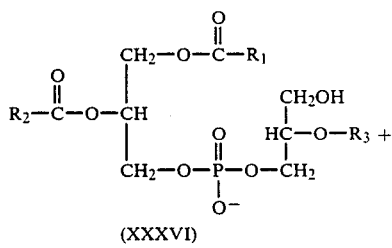

(XXXVI)

wherein R₁ and R₂ are hydrocarbon chains of 6-20 carbon atoms, saturated or unsaturated.

Liposomes containing propranolol or any other pharmaceutical agents are made with mixtures of phosphatidyl carnitine and other phosholipids and lipids. Examples are phosphatidylcarnitine, cholesterol (85:15) (molar ratios); phosphatidylcarnitine, phosphatidylcholine, cholesterol (20:70:10); phosphatidylcarnitine, cholesterol, stearylamine (50:10:40); phosphatidalcarnitine, phosphatidylserine, cholesterol (45:45:10).

Carnitine can also be added to liposomes by covalent linkage of carnitine to phospholipids with available functional groups. Then these derivatized phospholipids can be made into liposomes directly or mixed with other phospholipids and then made into liposomes.

Phosphatidylglycerol (XXXV), which is commercially available, can incorporate one (XXXVI) or two (XXXVII) moles of carnitine/mole of compound by reaction with sebacoyl dichloride (XXV).

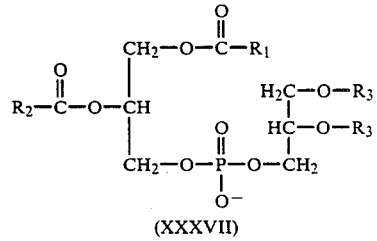

(XXXVII)

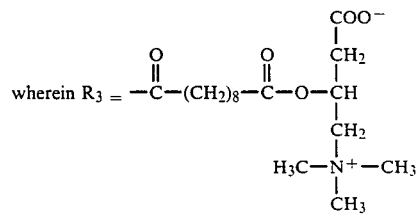

wherein $R_3 = $

Carnityl-ε-aminocaproate ester (V) can be linked to the amino group of phosphatidylethanolamine XXXVIII through a glutaraldehyde (V) condensation, or it can be linked to the carbonyl group of phosphatidylserine by a carbodiimide reaction (see below).

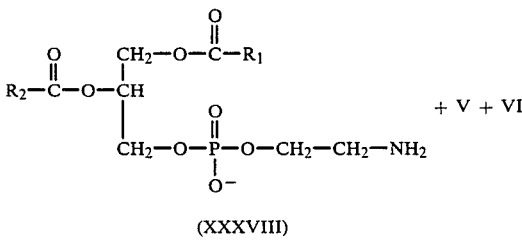

(XXXVIII)

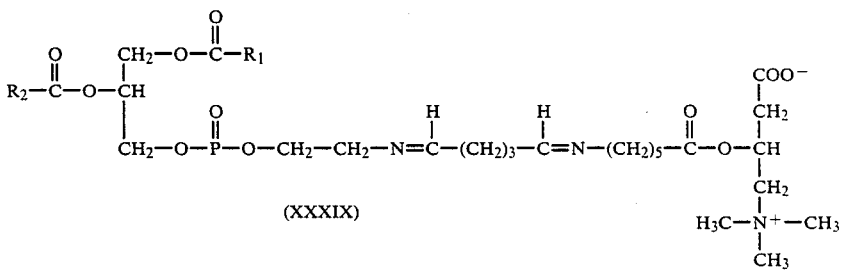

(XXXIX)

It may be advantageous to use NaCNBH₄ to convert this double Shiff's base (XXXIX) into its corresponding reduced form (XL) before using it further.

Aminocarnitine (IX) can be linked to the carboxyl group of phosphatidylserine (XLI) by a carbodiimide (CDI) reaction to form XLII or to phosphatidyletha-

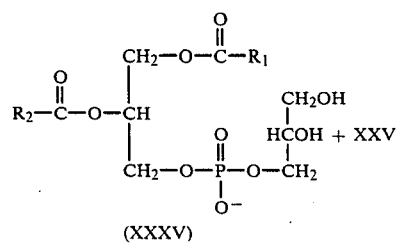

(XXXV)

nolamine (XXXVIII) through a glutaraldehyde condensation (see above reaction).

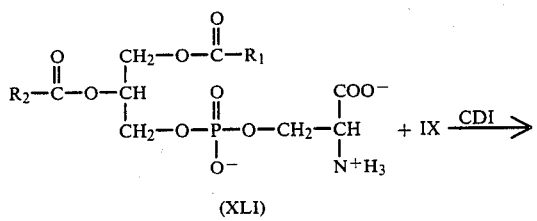

(XLI)

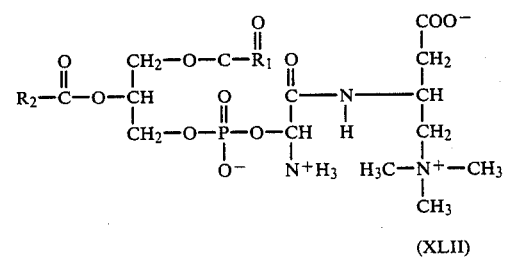

(XLII)

The carboxyl group on cysteic acid (XV) can be linked to the amino group of phosphatidylethanolamine (XXXVIII) or the amino group of phosphatidylserine (XLI) through a carbodiimide reaction.

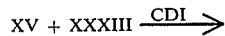

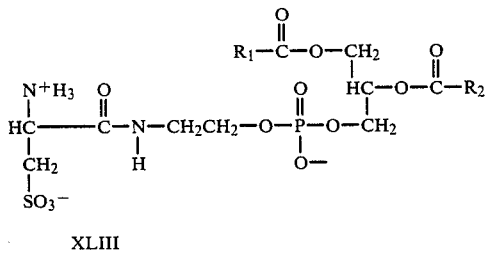

XLIII

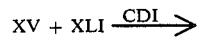

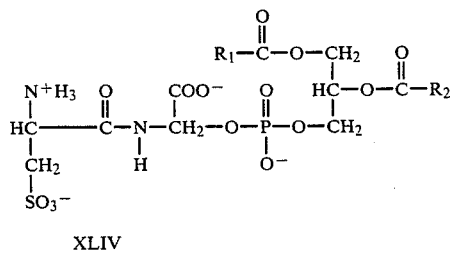

XLIV

In the past, a major drawback to the use of liposomes are vectors for drug delivery has been the fact that when injected into the blood stream they are taken up predominantly by the liver and reticuloendothelial system so that drugs active in disease conditions affecting other organs cannot be delivered efficiently by this procedure. In addition, liposomes cannot be administered orally because pancreatic lipase enzymes in the intestine break down the liposomes during digestion. The present invention offers a means of eliminating both of these drawbacks. Because of the presence of carnitine or aminocarnitine as part of the liposomal structure, the drug-containing liposomes will be delivered in much greater amounts to the desired target organs and much less will be metabolized by the liver. In addition, the presence of phosphatidyl carnitine in the liposome structure will present the intestinal lipase enzymes with a novel chemical structure that is apt to be far more resistant to digestion than naturally occurring lipids. This also holds true for liposomes containing amino carnitine and would serve to facilitate oral administration of organ specific pharmacologically active agents.

The specifications for such treatment vary with the type of clinical condition sought to be alleviated. For cases of severe arrhythmia, propranolol hydrochloride is usually administered intravenously (Goodman, L.S. and Gilman, A. G., *The Pharmacological Basis of Therapeutics*, 7th edition, Macmillan 1985, p. 197). Such a procedure is facilitated by using the drug in its site-directed, liposome-enveloped form. Thus, a suspension of phosphatidylcarnitine-linked liposomes loaded with a therapeutically effective dose (up to 3 mg) of propranolol hydrochloride in a total of 1 ml saline is injected intravenously into a patient suffering from severe arrhythmia. Blood pressure is then continually monitored with subsequent injections of propranolol-loaded liposomes as needed. This same procedure can be used effectively for other cardioactive drugs.

Propanolol has also been administered orally in doses of 40-320 mg per day to control arrhythmia and high blood pressure (Goodmand and Gilman, supra, p. 197). Although liposomes have heretofore been of little value in oral administration of drugs, the presence of phosphatidylcarnitine presents the inactivating intestinal lipases with a novel structure which will not be as readily degraded. Phosphatidylcarnitine-linked liposomes loaded with a physiologically effective dose of propranolol hydrochloride (or some other cardioactive substance) can be given orally in a slow-release capsule. After entering the bloodstream, the liposomes are directed, by the phosphatidylcarnitine structure, to be selectively taken up by the heart (to the exclusion of other organs).

In all cases, due to the phosphatidylcarnitineliposome enveloped form of the drug and the resulting site directed selectivity, lower doses of the drug can be employed (at lower cost) to achieve efficacious results while avoiding undesirable side effects on organs not requiring treatment.

It is believed the present invention may be useful for diminishing the damage incurred during cardiac ischemia resulting from the activation of calcium activated proteases.

Specifically, there is a great deal of evidence that the tissue damage resulting from myocardial ischemia is triggered by the influx of calcium ions into the myocyte. The elevated intracellular calcium levels then trigger a variety of responses such as activation of calcium activated proteases, phospholipases, and ATPases. If the ischemic condition proceeds, the damage becomes irreversible.

There are at least two important causes of myocardial damage due to calcium activated protease action. One is due to direct damage to myofilbrillar proteins (Sashida, H. and Abiko, Y., *Biochem. Pharm.* (1985) 34, 3875-3880). In addition, a calcium activated protease converts the enzyme Xanthine Dehydrogenase to Xanthine Oxidase. Xanthine Oxidase is a major source of oxygenderived free radicals in tissues. There is considerable evidence that these free radicals contribute to the damage seen during reprofusion. (Bernier, M., Hearse, D.J. and Manning, A. S., *Circulation Research* (1986) 58, 331–340.

Drugs that inhibit the influx of calcium into the myocardium such as nifedipine and verapamil, the so-called calcium entry blockers, protect against this problem. However, they are useful only if administered before or during early myocardial ischemia. The site-directed protease inhibitors can gain entry into the myocardium and inhibit enzymes which have already been activated.

It is not known if the materials act by hydrolysis to release the linked pharmaceutical after it has been delivered to the desired site or if the pharmaceutical functions in a linked state because its active groups are free to perform.

Because of the selective concentration at a particular site, it is possible to achieve at such sites a concentration of pharmaceutical which heretofore could have been achieved only by using a much higher overall dosage, perhaps such a high dosage as would be toxic or dangerous.

The linked materials are soluble in water or isotonic solution and can be administered to animals, human and otherwise, as well as to plants in any conventional manner, i.e., as solutions, tablets or capsules, depending upon the desired manner of administration, e.g., per os, injection, etc.

The carnitine is physiologically acceptable so the limiting factor on dosage is the pharmaceutical which, as already noted, can be a pharmaceutical precursor. Thus, for example, in administering carnityl leucyl argininal to chickens in accordance with the invention to enhance their growth by protease inhibition, about 1 mg/kg of body weight per day of linked compound VIII is useful, administered in the drinking water or admixed in the feed.

In general the dosage for animals may range from about 0.1 to 10 mg/kg/day in one dose or spread over several doses.

Fillers such as starch, cellulose, lactose, etc., may be admixed to facilitate dosage, and/or other active materials can be included.

The invention will be further described in the following illustrative examples wherein all parts are by weight unless otherwise expressed.

EXAMPLE 1

Preparation of Leucylarginal Dibutyl Acetal

Leupeptin (a mixture of N-acetyl and N-propionyl leucylleucylarginal) is converted to the chloride salt by passing it through a Dowes 1x8 (Cl$^-$) column. The material is eluted with water and fractions are collected. Each fraction is tested for leupeptin by thin layer chromatography on silica gel using the upper phase of the solvent mixture butanol-acetic acid water (4:1:5). Visualization is with iodine vapor. The fractions containing the leupeptin are combined and are evaporated to dryness on a Rotovap at room temperature.

The dry residue is taken up in butanol and refluxed for 2 hours. This produces the dibutyl acetals of leupeptin.

$$\text{Ac}-\overset{H}{N}-\text{leu}-\overset{O}{\underset{\|}{C}}-\overset{H}{N}-\text{leu}-\text{arg}\underset{\diagdown O\text{ But}}{\overset{\diagup O\text{ But}}{}}$$

An equal volume of butanol and double the volume of water are added in a separatory funnel. After extraction, the upper phase is removed and dried overnight with sodium sulfate. The solvent is then removed with a Rotovap.

To purify the acetals, they are separated on a silica gel column using a gradient starting with chloroform and ending with 60% butanol/chloroform. The purified N-propionyl and N-acetyl forms are identified by thin layer chromatography as described above. The fractions are pooled and evaporated to dryness.

Cleavage of the N-propionyl and N-acetyl leucine is accomplished by reaction with the enzyme thermolysin. This is done at pH 8, over a 72 hour incubation period. The reaction is followed by measuring the release of free amino groups by the TNBS reaction.

$$\text{Ac}-\overset{H}{N}-\text{leuCOO}^- + \text{H}_2\text{N leuarg}\underset{\diagdown O\text{ But}}{\overset{\diagup O\text{ But}}{}}$$

(VII)

The leucylarginal dibutyl acetal is isolated from this mixture by chromatography on a silica gel column as previously described. The fractions are identified by thin layer chromatography and the solvent is removed. The dry residue is stored in the freezer.

EXAMPLE 2

Preparation of Carnityl-ε-Amino Caproate Ester

The acid chloride of ε-aminocaproic acid is formed by reaction with oxalyl chloride at 0° C.

$$\text{H}_2\text{N}-(\text{CH}_2)_5-\text{COOH} + (\text{COCl})_2 \longrightarrow \text{H}_2\text{N}(\text{CH}_2)_5-\underset{\underset{O}{\|}}{C}-\text{Cl}$$

(II)          (IV)

Excess oxalyl chloride is evaporated off and the acid chloride is then dissolved in acetonitrile. Solid carnitine is then added and the ester (V) is formed. The solvent is removed by evaporation.

EXAMPLE 3

Coupling by the Carbodiimide Method

One way of coupling the leucylarginal to the ester is through the carbodiimide reaction.

Glutaric acid (1 mMol) is reacted with 2 equivalents of 1-ethyl-3-(3-dimethyl aminopropyl) carbodiimide (CDI)

$$\text{CH}_3-\text{CH}_2-\text{N}=\text{C}=\text{N}-\text{CH}_2-\text{CH}_2-\text{CH}_2-\text{N}\underset{\diagdown \text{CH}_3}{\overset{\diagup \text{CH}_3}{}}$$

in 2 ml H$_2$O at room temperature for 20 minutes to produce $$\begin{array}{c}\text{R}_1\text{NH} \quad\;\; \text{O} \quad\quad\quad\;\; \text{O} \quad\, \overset{H}{N}-\text{R}_1 \\ |\quad\quad\;\; \| \quad\quad\quad\quad \| \quad\;\; | \\ \text{HC}-\!\!-\text{C}-(\text{CH}_2)_3-\text{C}-\!\!-\text{CH} \\ |\quad\quad\quad\quad\quad\quad\quad\quad\quad\; | \\ \text{R}_2\text{N} \quad\quad\quad\quad\quad\quad\quad\;\; \text{NR}_2 \\ \quad\quad\text{H}\end{array}$$

To this is added 1 equivalent of leucylarginal dibutylacetal.

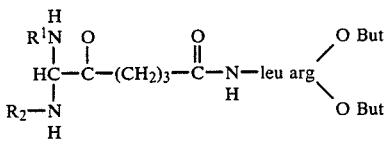

This is followed by 1 equivalent of carnityl-ε-aminocaproate

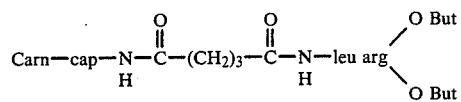

The substance is partially purified by chromatography on a Sephadex G10 column. Elution is with water and fractions are tested for trypsin inhibition activity before and after hydrolysis at pH 2, 60° C. for 3 hours. The fractions with activity are neutralized, evaporated to dryness and checked for purity by thin layer chromatography.

It has been shown that in vitro carnitylleucylargininal inhibits Ca-activated protease as well as leupeptin, viz.

|  | % of Control |
|---|---|
| Control | 100 |
| Control + carnitine (100 ug) | 84 |
| Control + leupeptin (100 ug) | 7.9 |
| Control + carnitylleucylargininal (100 ug) | 4.6 |

The following table shows the effect of hydrolysis of carnitylleucylargininal dibutylacetal (100ug) at 60° C., pH 2 on the ability to inhibit Ca-activated protease in vitro:

|  | % of Control |
|---|---|
| Control | 100 |
| 0 time | 17 |
| 3 hours | 1.2 |
| 24 hours | 100 |

These results show that the dibutylacetal has some Ca-activated protease inhibitory activity. At the end of 3 hours, hydrolysis of the acetals has produced a stronger inhibitor. After 24 hours of hydrolysis, all inhibitory activity has been destroyed.

The following table shows the effect of in-vivo administration on the ability to inhibit muscle Ca-activated protease (2 hours post IP injection):

|  | % Inhibition |
|---|---|
| Control | 0 |
| leupeptin (74 umoles) | 20 |
| carnitylleucylargininal (19 umoles) | 48 |

These results show that carnitylleucylargininal, when injected into rats, is about ten times more effective per umole then leupeptin in inhibiting Ca-activated protease in skeletal muscle.

The following results were obtained for inhibition of platelet Ca-activated protease:

| Final in-vitro conc. (1 mM) | % Inhibition |
|---|---|
| Cysteic acid (CDI treated) | 0 |
| E-aminoadipic acid (CDI treated) | 0 |
| leucylargininal | 94 |
| leupeptin | 98 |
| cysteicleucylargininal | 98 |

These results show that the cysteic acid derivative of leucylargininal retains full protease inhibitory activity.

It will be understood that the specification and examples are illustrative but not limitative of the present invention and that other embodiments within the spirit and scope of the invention will suggest themselves to those skilled in the art.

EXAMPLE 4

Preparation of Phosphatidylcarnitine (XXXIV)

10 mmoles of l-carnitine (I) are dissolved in 40 ml dry dimethylformamide (DMF). The solution is warmed to 60° C. and to this is added 10 mmoles of chloromethylphthalimide (XLV). The temperature is maintained at 60° C. for 24 hours under an atmosphere of nitrogen. The volume is then reduced under reduced pressure and the mixture is placed on a 1.8 x 40 cm silica gel column. A gradient starting with chloroform and linearly increasing in methanol content is pumped through the column and 10 ml fractions are collected. The tubes containing the product are detected by thin layer chromatography on silica gel G plates with butanol acetic acid water (4:1:1) as solvent and iodine vapor as detecting agent.

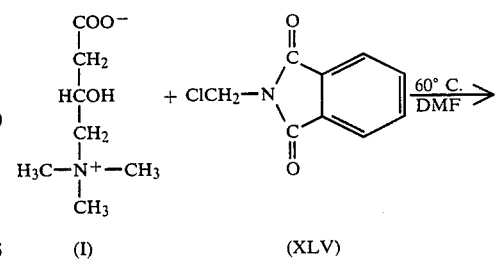

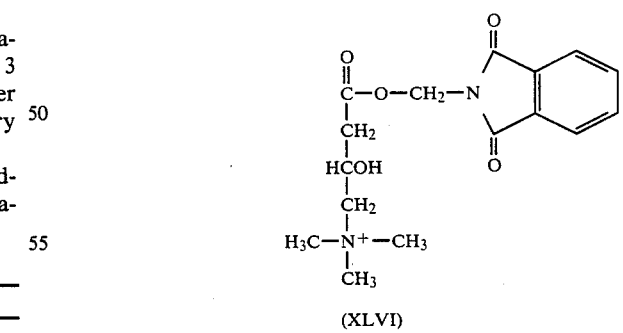

Phosphatidic acid (XLVII) of desired fatty acid composition, optical activity and many other characteristics is commercially available. 1 mmole is dissolved in 6 ml dry chloroform and to this is added 2 ml dry pyridine and 4 mmoles 2,4,6-triisopropylbenzenesulfonyl chloride (TSC) used as the condensing agent. To this is added 2 mmoles of carnitine phthalimidomethyl ester (XLVI). The reaction mixture is kept at 40° C. for 3 hours after which the mixture is reduced to a small volume under reduced pressure. The entire mixture is applied to the top of a 1.8 x 20 cm silica gel column and the product is eluted by pumping a solvent gradient containing dichloroethane and increasing in concentrations of methanol. The tubes containing the product are identified by thin layer chromatography as described above.

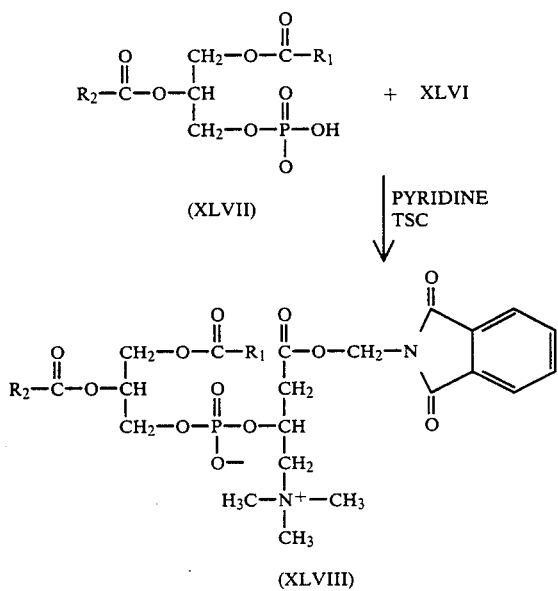

0.5 mmole of (XLVIII) are dissolved in 5 ml dry DMF and 1.5 mmole of sodium thiophenoxide are slowly added with stirring to cleave the ester bond. The solution is concentrated to a small volume under reduced pressure and applied to the top of a 1.8 x 20 cm silica gel column. A chloroform methanol gradient is pumped through the column and the tubes containing the product are identified by thin layer chromatography as previously described.

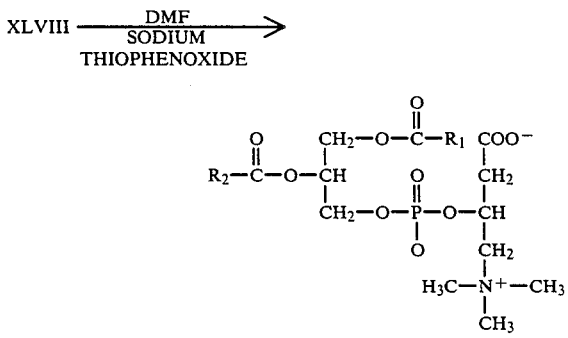

EXAMPLE 5

Preparation of Liposome containing phosphatidylcarnitine which encapsulate propranolol Liposomes are prepared by standard procedures. Thus 5 mg phosphatidylcarnitine is dissolved in 1 ml chloroform-methanol (2:1) in a small glass tube. To this solution is added 2 mg propranolol and the mixture of nitrogen gas and to the dry film is added 1 ml phosphate buffer pH 7.4, 0.01 M. The tube is sonicated in 200 Watt bath type sonicator for 15 minutes at room temperature. The contents are then filtered through a 1.2 um membrane filter and the liposomes are separated from the unencapsulated propranolol by chromatography on a 0.9×20 cm Sepharose 6B column.

What is claimed is:

1. A compound comprising aminocarnitine covalently bonded through an alcohol, carboxyl or amine group to a pharmaceutically active compound.
2. A compound according to claim 1, wherein the pharmaceutically active compound is a protease inhibitor.
3. A compound according to claim 1, wherein the pharmaceutically active compound is pepstatin or leucylargininal.
4. A pharmaceutical composition preferentially deliverable to cardiac and skeletal muscle comprising a pharmaceutically effective amount of the compound of claim 3 effective therefor and a pharmaceutically acceptable diluent.
5. A compound according to claim 1, wherein the pharmaceutically active compound is cardioactive.
6. A compound according to claim 1, wherein the active compound is active against arrythmia.
7. A pharmaceutical composition preferentially deliverable to cardiac and skeletal muscle comprising a pharmaceutically effective amount of the compound of claim 6 effective therefor and a pharmaceutically acceptable diluent.
8. A compound according to claim 1, wherein the bond is through a bifunctional radical.
9. A compound according to claim 1, wherein the bond is through at least on bifunctional radical of a dialdehyde, carbodiimide, dicarboxylic acid or aminoacid.
10. A compound according to claim 1, wherein the pharmaceutically active compound is procainamide.
11. In the treatment of a muscle disorder in a patient wherein a pharmaceutically active compound is administered to such patient, the improvement which comprises administering said compound covalently bonded through an alcohol, carboxyl or amine group to aminocarnitine.
12. The method according to claim 11, wherein the muscle being treated is a skeletal muscle.
13. The method according to claim 12, wherein the pharmaceutically active compound is a protease inhibitor.
14. The method according to claim 11, wherein the muscle being treated is the heart.
15. The method according to claim 14, wherein the pharmaceutically active compound is active against arrythmia.
16. The method according to claim 11, wherein the pharmaceutically active compound is procainamide.

* * * * *